United States Patent [19]
Kamienski et al.

[11] Patent Number: 5,523,447
[45] Date of Patent: Jun. 4, 1996

[54] ORGANOLITHIUM PROCESS

[75] Inventors: Conrad W. Kamienski, Gastonia; James A. Schwindeman, Lincolnton; B. Troy Dover, Kings Mountain; Robert C. Morrison, Gastonia, all of N.C.

[73] Assignee: FMC Corporation, Philadelphia, Pa.

[21] Appl. No.: 477,843

[22] Filed: Jun. 7, 1995

[51] Int. Cl.$^6$ .............................. C07F 7/08; C07F 7/18; C07F 1/02; C07F 1/04

[52] U.S. Cl. .................. 556/466; 556/482; 556/485; 260/665 R; 568/671

[58] Field of Search ........................ 556/482, 485, 556/466; 260/665 R; 568/671

[56] References Cited

U.S. PATENT DOCUMENTS

| | | | |
|---|---|---|---|
| 5,211,887 | 5/1993 | Morrison et al. | 260/665 R |
| 5,211,888 | 5/1993 | Morrison et al. | 260/665 R |
| 5,321,148 | 6/1994 | Schwindeman | 556/466 |
| 5,331,058 | 7/1994 | Shepherd et al. | 525/332.3 |
| 5,332,533 | 7/1994 | Schwindeman et al. | 260/665 R |
| 5,340,507 | 8/1994 | Morrison et al. | 260/665 R |
| 5,362,699 | 11/1994 | Shepherd et al. | 502/158 X |
| 5,376,745 | 12/1994 | Handlin, Jr. et al. | 526/178 |
| 5,378,761 | 1/1995 | St. Clair | 525/111 |
| 5,391,637 | 2/1995 | Willis et al. | 525/385 |
| 5,391,663 | 2/1995 | Bening et al. | 526/178 |
| 5,393,843 | 2/1995 | Handlin, Jr. et al. | 525/332.8 |
| 5,403,946 | 4/1995 | Schwindeman | 556/466 |
| 5,416,168 | 5/1995 | Willis et al. | 525/333.2 |

*Primary Examiner*—Paul F. Shaver
*Attorney, Agent, or Firm*—Charles C. Fellows; Robert L. Andersen

[57] ABSTRACT

A process for preparing easily separable solutions of organolithium compounds comprising the steps of reacting lithium metal, in the form of cast or extruded ingots or pieces cut therefrom, with an organo halide in mole ratios ranging from 3:1 to 20:1 in a solvent selected form a group of liquid hydrocarbons, alkyl ethers, and mixtures thereof under an inert atmosphere for one to ten hours with moderate stirring, cooling the resulting product, and separating the solution of the organolithium compound from the reacted lithium metal and by-product lithium chloride in the reactor.

17 Claims, No Drawings

ORGANOLITHIUM PROCESS

This invention concerns a process for producing organolithium compounds from organo halides and lithium metal used as cast or extruded ingots or pieces cut therefrom which will be defined herein as bulk metal and certain novel organolithium compositions.

In co-pending application U.S. Ser. No. 129818 filed Sep. 30, 1994, there is described a process for preparing clear suspensoid-free solutions of lithium tert-butoxide in ethereal or hydrocarbon solvents by reaction of lithium metal in bulk form with a limiting quanity of tert-butyl alcohol. In another co-pending application U.S. Ser. No. 08/204,724 filed Mar. 2, 1994, there is described a process for preparing lithium alkylamides by reacting lithium metal in bulk form with an alkyl amine in mixed ethereal/hydrocarbon solution.

The preparation of organolithium compounds by the direct reaction of organo halides with lithium metal is well known. The reactions are conducted in hydrocarbon or ethereal solvents depending on the selected organolithium. Phenyl halides, methyl halides, alkenyl halides and some heteroatom-containing organo halides require ethereal solvents due to the low solubility of the resulting organolithium compounds in hydrocarbon solvents. It is well known that, although the more costly bromides and iodides of the above mentioned halides can be reacted successfully with bulk (as defined above) sizes of lithium metal in stochiometric or near stoichiometric amounts in ethereal solvents to yield the desired organolithium compounds, the respective organo chlorides are slow to react and require lithium metal in a comminuted or dispersed form for successful conversions. Such dispersed forms of lithium metal are also required for the preparation of $C_3$ to $C_{18}$ alkyllithiums in good yields, in hydrocarbon solvents. Although bulk metal in stochiometric amounts can be used to prepare these alkyllithiums from both $C_3$ to $C_{18}$ alkyl chlorides and bromides in ethereal solvents, the temperatures must be kept prohibitively low (0° C.) to prevent attack of the resulting alkyllithium on the solvent. Reactions of the latter organo halides with stoichiometric bulk metal in hydrocarbon solvents are slow and reactions do not go to completion.

Although lithium metal in a finely dispersed state reacts rapidly with $C_3$ to $C_{18}$ alkyl halides in hydrocarbon media such lithium dispersions are costly to produce, requiring the steps of (a) heating of bulk lithium metal and mineral oil to about 190°–200° C. in the presence of a dispersion aid, such as oleic acid, (b) stirring the resultant molten mixture at high speeds in a special dispersion unit to produce the required small particle sizes (generally less than 100 microns), then (c) cooling the product (preferably without stirring), and then finally (d) removing the mineral oil from the solidified lithium metal particles by washing several times with a volatile hydrocarbon solvent, such as hexane or pentane. The volatile hydrocarbon solvent can optionally be removed by purging with an inert gas such as argon, or more preferably, be washed one or more times with the reaction solvent before reaction with the alkyl halide.

Besides being costly to produce, lithium dispersion also may add undesirable impurities, such as, e.g., mineral oil and oleic acid breakdown products, and volatile hydrocarbons to the subsequent organolithium product dissolved in etheral or hydrocarbon solvent media which are known to contribute to the generation of color in the solutions of product organolithiums. Lithium dispersions are also pyrophoric when the protective oil is removed and therefore hazardous to work with, whereas, bulk lithium can be handled in air without protective coatings.

Because of the extremely small sizes of the lithium dispersion metal particles, a high proportion of solid impurities, small in size may also be present after reaction with organo halide is complete. Impurities on the lithium surface slow down the initial reaction and may lower yield of organolithium. These impurities arise from side reactions with traces of oxygen in the inert atmosphere, of traces of water in the solvent and alkylhalide and with the solvent itself. These small solid impurities (including any unreacted lithium metal particles) cause filtration problems.

The present invention provides a process for quickly preparing in high yield, easily separable solutions of organolithium compounds in an economically feasible time period of 1 to 10 hours, comprising the steps of reacting lithium metal in bulk form ["Bulk" form is defined above as cast lithium metal ingots, obtained from manufacture in an electrolytic cell, without further remelting in a hydrocarbon oil to effect comminution thereof by means of some form of agitation. The bulk lithium metal may be further reduced in size by an extrusion process and/or subsequent cutting into smaller, more manageable pieces or even by directly slicing the cell "ingot" into smaller pieces but generally not smaller than 0.5grams per piece], with an organohalide in mole ratios of lithium metal to organo halide ranging from 3 to 1 to 20 to 1 in an ethereal or hydrocarbon medium or mixtures thereof under an inert atmosphere at ordinary or elevated temperatures, cooling the product and separating the product from the unreacted lithium metal in the reactor. The process is conveniently continued by adding additional solvent, sufficient lithium metal and organohalide to the unreacted excess metal in the reactor to maintain the mole ratio of lithium metal to organohalide, and continuing the reaction, thereby to form further organolithium, and repeating said steps a number of times.

Unexpectedly, the process of the present invention overcomes problems experienced with the use of lithium metal in a finely divided (dispersed) state without experiencing a great increase in reaction time by the use of a sufficient excess of lithium metal in bulk form (over and above the alkylhalide used). Surprisingly, the amount of lithium metal in bulk form needed to preserve a comparable overall reaction time when compared to lithium in dispersed form is only in the order of about two to ten times.

For example, the surface area of one gram equivalent of lithium metal particles 20 microns in diameter is about 13,000 square centimeters, while the surface area of an equivalent amount of lithium metal cubes with dimensions of one centimeter by one centimeter by one centimeter is only 79 square centimeters, a one hundred sixty-six times greater surface area for the dispersed lithium. One would therefore expect the relative amount of lithium in bulk form needed to give a overall reaction rate comparable to the dispersed lithium to be in the order of one hundred sixty-six times greater. Instead, only about three to twenty equivalents (237 to 1580 sq cm) of lithium metal in the form of rod cylindrical pieces was found to react with one equivalent of organohalide in a comparable overall reaction time (2–3 hours) as did one equivalent of lithium metal dispersed to 20 micron diameter particles (about 1–2 hours). For example the following table (1) depicts the synthesis of 36 weight percent n-butyllithium in hexane at reflux using varing ratios of bulk metal to n-butyl chloride compared to lithium dispersion.

TABLE 1

Synthesis of n-Butyllithium in Hexane

| Run | Li mole | n-BuCl moles | Li/n-BuCl mole ratio | S.A.Li† sq cm | S.A.Li/Mo sq cm[b] | S.A.Li(bk)/ sq cm[c] | Yield % |
|---|---|---|---|---|---|---|---|
| 8920 | 3.4 | 1.5 | 2.2 | 43967 | 28811 | 1.00 | 95.1 |
| 9053 | 10.1 | 0.5 | 20 | 975 | 1933 | 0.20 | 99.2 |
| 9020 | 10.1 | 1.0 | 10 | 975 | 967 | 0.10 | 95.7 |
| 9048 | 10.1 | 1.7 | 6 | 975 | 580 | 0.06 | 91.4 |
| 9071 | 10.1 | 1.0 | 10 | 479 | 475 | 0.05 | 92.6 |
| 9038 | 10.1 | 1.0 | 10 | 284 | 282 | 0.03 | 87.8 |

[a] Surface area of the lithium in square centimeters.
[b] Surface area of the lithium divided by the moles of n-butyl chloride in square centimeters.
[c] Surface area of bulk lithium divided by the surface area of lithium dispersion in square centimeters.

The above table shows that only one tenth of the surface area of lithium dispersion in the form of bulk metal is needed to produce equivalent yield of n-butyllithium.

The ease of separation of the product solution from unreacted lithium metal is maintained in each subsequent run and there is no hazardous unreacted lithium in with the lithium chloride to be disposed of as in the runs using dispersed lithium.

A non-obvious useful variant of the above separation procedure in the case of n-butyllithium preparations is as follows: The mixture of lithium metal and hydrocarbon solvent is not stirred during reaction with n-butyl chloride. This procedure maintains adherence of the layers of by-product lithium chloride formed on to the surface of the lithium metal and facilitates rapid separation of the final product solution from the metal pieces by filtration or decantation. After removal of the product solution, the metal pieces are stirred vigorously with fresh solvent to dislodge the adherent lithium chloride and the resultant slurry of salt particles separated from the floating metal pieces. The salt slurry may be further treated by filtration or decantation, followed by drying and recycle or by simply dissolving the inert by-product lithium chloride in water, separation of the liquid layers and recycle. It should be noted that the first option produces a salt which contains no entrained lithium metal as occurs with the use of lithium dispersion and is safe to handle, and the second option generates no flammable hydrogen gas for the same reason. Besides the element of safety and evironmental concerns, there is an element of economy in the inventive process since no loss of expensive lithium metal occurs as does when lithium dispersions are used, where entrained metal is present in the by-product lithium chloride. This entrained metal loss can be substantial, since not only is there a loss of the usually employed 5 to 20 percent excess lithium in the latter process, but there is a loss of any metal left over due to realization of less than quantitative product yields. Such losses of lithium metal do not occur in the inventive process.

Other approaches than vigorous stirring remove the lithium halride from the surface of the reacted lithium in bulk form involve vibratory techniques and treatment with solvating agents for the lithium chloride which are non-reactive to lithium metal. Examples of such solvents are ethers such as, e.g. tetrahydrofuran, dimethoxyethane and diethoxyethane, as well as other solvents such as, e.g., propylene carbonate, dimethyl sulfoxide, dimethylacetamide, hexamethylphosphoramide and dimethylformamide.

When the solvating agent for lithium chloride is also a good solvent for the salt, one may envision the use of a fixed bed static system such as a column packed with lithium metal in bulk form.

Other unexpected benefits occur from the use of bulk metal as compared to lithium dispersions. For example, lighter colored product solutions of n-butyllithium in hydrocarbon solvents are produced, presumably due to the absence of impurities present in the lithium dispersion preparation. At high product yields (95 to 99 percent), colorless, water clear, solutions of n-butyllithium are obtained with the use of bulk lithium metal, presumably also due to the absence of olefinic by-product impurities.

Another unexpected advantage realized when bulk lithium metal is employed is the ability to obtain high product yields of alkyllithium, such as n-butyllithium, in hydrocarbon solution at very high product concentrations, in the order of 50 to 60 weight percent preferebly even and higher, up to 90 weight percent.

It is quite unexpected that the size of the lithium metal pieces used in in the reaction with organo halides in ethereal or hydrocarbon mixtures can be varied widely, depending on the batch size of the runs, without unduly increasing the overall reaction time. Thus, any of the common commercially available sizes of lithium metal may be employed or segments [pieces] may be cut from these.

Sizes of bulk lithium metal available commercially which can be used are: one inch (2.5cm) diameter by 8 inch (20.3 cm) long rods, one-half inch (1.3 cm) by 6.5 inch (16.5 cm) long rods, 2.25 inch (5.7 cm) by 3.38 inch (8.6cm) long cylindrical ingots [¼ lb], 3 inch (7.6cm) diameter by 3.8 inch (9.7 cm) long cylindrical ingots [½ lb (227 g)] , 4 inch (10.2cm) diameter by 5 (12.7 cm) inch long cylindrical ingots [1 lb (454 g)], and two pound (908 g) trapezoidal ingots having dimensions of 2.5/3.5 inches (6.4/8.9 cm) in width by 3.25 inches (8.3 cm) in height by 10.5 inches (26.7 cm) in length.

The optimum size of the lithium metal employed will depend upon the size of the reaction being carried out with larger pieces generally used in the larger size reactions. Generally, the size of the pieces of lithium being employed will be such that the overall reaction time will be less than 8–10 hours. The minimum size pieces of metal should be easily visible as being discrete particles, i.e., not particles produced by a dispersion process as described above [less than 0.1 millimeter] and should generally weigh at least 0.5 gr per piece.

Generally, it is preferable to use excesses of such bulk metal relative to the alkylhalide in the range of 3:1 to 20: 1, depending on the nature of the organo halide and solvent.

Solvents which may be used in the process of this invention are chosen from the group of liquid hydrocarbons such as, e.g. pentane, hexane, heptane, benzene, toluene and cyclohexane, and from the group of liquid alkyl ethers, such as, e.g., ethyl ether, dibutyl ether, methyl-t-butyl ether, tetrahydrofuran, methyltetrahydrofuran, diethoxymethane, dimethoxyethane and mixtures of members taken from both groups. Generally, solvents are chosen which permit the desired organolithium to be substantially soluble in the medium. Thus, for example, methyllithium is prepared in ethyl ether or in diethoxymethane, phenyllithium in diethyl ether or dibutyl ether and $C_3$ to $C_{18}$ alkyllithiums in liquid hydrocarbons.

Reaction temperatures can be varied widely depending to a large degree on the boiling point of the solvent chosen. Thus, methyllithium and phenyllithium are prepared in ethyl ether at about 30°–35 ° C. while n-butyllithium is prepared in hexane at 70 ° C. (reflux). Generally reaction temperature can be chosen from about 20 ° C. to about 100 ° C., depending on the solvent type. However, it is not necessary to employ solvents at the boiling point, and lower reaction temperatures can be employed.

Organolithiums which can be prepared by the inventive process may be chosen from the group of alkyllithiums, such as methyllithium, ethyllithium, n-propyllithium, n-butyllithium, s-butyllithium, t-butyllithium and n-hexyllithium, from the group of aryllithiums such as phenyllithium and the tolyllithiums and from the group of heteroatom containing organolithium compoumds such as 2-thienyllithium, 1-methyl-2-piperidyllithium,2-furyllithium,3-(t-butyldimethylsilyloxy)propyl-1-lithium, 3-(t-butoxy)propyl-1-lithium, and 3-(trimethylsilyloxy)2,2-dimethyl-propyl-1-lithium.

Organo halides may be chlorides, bromides or iodides, but most preferably chlorides. Organohalides useful in practicing the present invention include but are not limited to methylhalide, ethylhalide, n-propylhalide, n-butylhalide, s-butylhalide, t-butylhalide and n-hexylhalide, from the group of arylhalides such as phenylhalide and the tolylhalides and from the group of heteroatom containing organohalide compoumds such as 2-thienylhalidem, 1-methyl-2-piperidylhalide,2-furylhalide, 3-(t-butoxy)propyl- 1-halide, (3-t-butyldimethylsilyloxy)propyl-1-halide, and 3-(trimethylsilyloxy)-2,2-dimethyl-propyl-1-halide.

COMPARISON EXAMPLE (8920)Synthesis n-Butyllithium in Hexane Employing Lithium Dispersion To a reactor equipped as in example 1 under an argon atmosphere was placed 23.3 grams (3.36 moles) of lithium powder (10 percent excess) obtained by removal of the mineral oil from a lithium dispersion and then drying the metal, and 261 milliliters of dry hexane. The lithium metal had a surface area of 44,000 $cm^2$ and the mole ratio of lithium to n-butyl chloride was 2.2. The mixture was stirred and heated to reflux, at which point n- butyl chloride (140.1 grams, 1.51 moles) was added dropwise over a one hour period, while controling the reflux rate with external cooling. Samples of the reaction mass were taken periodically during the addition, and monitored by GC of water quenched samples for the presence of n-butyl chloride. The n-butyl chloride concentration was always well below 0.01 molar. After allowing the reaction mass to cool (approx. 1 hour), the reaction mass was filtered and the solids washed with dry hexane to yield 408.9 grams of a clear product solution. Analysis of the solution showed the presence of 22.54 weight percent n-butyllithium for a recovered yield of 95 percent.

COMPARISON EXAMPLE (8278)Synthesis of sec-Butyllithium in Hexane Employing a Lithium Dispersion To a reactor equipped as in example 1 under an argon atmosphere was placed 15.1 grams (2.17 moles) of lithium powder (10 percent excess) obtained by removal of the mineral oil from a lithium dispersion and then drying the metal, and 257 milliliters of dry hexane. The lithium metal had a surface area of 44,000 $cm^2$ and the mole ratio of lithium to n-butyl chloride was 2.2. The mixture was stirred and heated to reflux, at which point sec- butyl chloride (91.7 grams, 0.99 moles) was added dropwise over a 51 minutes, while controling the reflux rate with external cooling. After allowing the reaction mass to cool (approx. 1 hour), the reaction mass was filtered and the solids washed with dry hexane to yield 370.5 grams of a clear product solution. Analysis of the solution showed the presence of 15.2 weight percent sec-butyllithium for a recovered yield of 89 percent.

EXAMPLE 1

(9053)Synthesis n-Butyllithium in Hexane Employing Bulk Lithium—Stirred Reaction A reactor equipped with a reflux condenser, a temperature indicating device, an addition funnel for adding liquid materials to the reactor, an external heating mantle, a source of argon for maintaining an inert atmosphere and a mechanical stirrer was charged with 70 grams (10.08 moles) of lithium metal in the form of 0.635 cm×1.905 cm rod (220 pieces) and 91 milliters of dry hexane. The surface area of the lithium metal was calculated to be 975.4 cm2 and the mole ratio of lithium to n-butyl chloride was 20. In the addition funnel were placed 46.3 grams of n- butyl chloride and the reactor and contents were heated with the heating mantle until the hexane was at reflux (66.8 ° C.). The reaction mass was moderately stirred throughout halide addition and post reaction times. Addition of 2 milliters of the n-butyl chloride brought about a vigorus reflux within 5 minutes which indicated initiation of reaction. The remaining n-butyl chloride was added dropwise to the reactor in 125 minutes. The exothermic reaction of halide with the lithium maintained the internal reaction temperature at reflux throughout the halide addition. The internal temperature gradually rose from 66.8° to 70.6 ° C. during this time period. The reaction mass was stirred during an additional 30 minutes of post reaction time. The liquid portion of the reaction mass containing by-product lithium chloride was pressure pumped to a filter and then filtered. The metal remaining in the reactor was washed with 150 and 100 milliliter aliquots of dry hexane which were also filtered and then combined with the main filtrate. The unused lithium in the reactor was left for further reactions.

A total weigh of 237 grams of a near water white solution of 12.8 wt % n-butyllithium was obtained. The recovered yield was near quanitative (99.2%) based on the amount of n-butyl chloride employed. The reaction was periodically monitored by GC of water quenched samples for side reaction formation and residual n-butyl chloride during addition and post reaction. The GC conversion based on octane was 99.6% and about 3% unreacted n-butyl chloride was present during the course of reaction. No n-butyl chloride was present after the post reaction time. and 98% of the n-butyl chloride had reacted during the halide addition period.

EXAMPLE 2

(9071 )Synthesis n-Butyllithium in Hexane Employing Bulk Lithium—Stirred Reaction To a reactor equipped as described in example 1 under an argon atmosphere was charged with 70.3 grams ( 10.12 moles) of lithium metal in the form of 0.5 cm dia×5.08 cm length rod (21 pieces) and 173 milliliters of dry hexane. The surface area of the lithium metal was calculated to be 479 cm2 and the mole ratio of lithium to n-butyl chloride was 10. Normal butyl chloride (92.6 grams-1.0 mole) were placed in the addition funnel and the reactor and contents were heated with the heating mantle until the hexane was refluxing (66.6° C.).The reaction mass was moderately stirred throughout halide addition and post reaction times. Addition of 3 milliliters of the n-butyl chloride brought about a vigorous reflux within 15 minutes which indicated initiation of reaction. The remaining n-butyl chloride was added dropwise to the reactor in 120 minutes. The exothermic reaction of halide with the lithium maintained the internal reaction temperature at reflux throughout the halide addition. The reaction mass was stirred an additional 150 minutes of post reaction time. The internal temperature gradually rose from 66.6° to 71.2 ° C. during the reaction time. The liquid portion of the reaction mass containing by-product lithium chloride was pressure pumped to a filter and then filtered. The metal remaining in the reactor was washed with 60 and 50 milliliters each aliquots of dry hexane which was also filtered and then combined with the main filtrate. The unused lithium in the reactor was left for further reactions.

A total weight of 338 grams of a light yellow solution of 16.11 wt % n-butyllithium was obtained. The recovered yield was 92.6% based on the amount of n-butyl chloride employed. The reaction was periodically monitored by GC of water quenched samples for side reaction formation and residual n-butyl chloride during the reaction. The GC conversion based on octane was 94.5% and from about 7 to 14% of unreacted n-butyl chloride was present during the course of the halide feed. No n-butyl chloride was present the after post reaction time period.

EXAMPLE 3

(9038)Synthesis n-Butyllithium in Hexane Employing Bulk Lithium—Stirred Reaction To a reactor equipped as described in example 1 under an argon atmosphere was charged with 70.8 grams ( 10.2 moles) of lithium metal in the form of 2.54 cm dia×3.81 cm length rod (7 pieces) and 173 milliliters of dry hexane. The surface area of the lithium metal was calculated to be 283.8 cm2 and the mole ratio of lithium to n-butyl chloride was 10. In the addition funnel was placed 92.57 grams (1.0 moles) of n- butyl chloride and the reactor and contents were heated with the heating mantle until the hexane was at reflux (66.7° C.). The reaction mass was moderately stirred throughout the halide addition and post reaction times. A dropwise addition of n-butyl chloride was begun which brought-about a vigorous reflux within 15 minutes which indicated initiation of reaction. The remaining n-butyl chloride was added dropwise to the reactor in 120 minutes. The exothermic reaction of halide with the lithium maintained the internal reaction temperature at reflux throughout the halide addition. The reaction mass was stirred an additional 330 minutes of post reaction time. As product formed the internal temperature gradually rose from 66.7° to 71.8 ° C. during the reaction time. The liquid portion of the reaction mass containing by-product lithium chloride was pressure pumped to a filter and then filtered. The metal remaining in the reactor was washed with two 100 milliliter aliquots of dry hexane which was also filtered and then combined with the main filtrate. The unused lithium was left in the reactor for further reactions.

A total weight of 353 grams of a light yellow solution of 15.92 wt % n-butyllithium was obtained. The recovered yield was 87.8% based on the amount of n-butyl chloride employed. The reaction was periodically monitored by GC of water quenched samples for side reaction formation and residual n-butyl chloride during the reaction. The GC conversion based on octane was 89.0% and an almost constant amount (16% of the feed) of unreacted n-butyl chloride was found to be present during the halide feed. Eighty four percent of the total amount of n-butylchloride employed had reacted during the halide addition. No n-butyl chloride was present after the post reaction time period.

EXAMPLE 4

(9048) Synthesis n-Butyllithium in Hexane Employing Bulk Lithium—Stirred Reaction To a reactor equipped as described in example 1 under an argon atmosphere was charged with 70.4 grams (10.1 moles) of lithium metal in the form of 0.635 dia×1.905 cm length rod (220 pieces) and 301 milliliters of dry hexane. The surface area of the lithium metal was calculated to be 975.4 cm2 and the mole ratio of lithium to n-butyl chloride was 6. In the addition funnel were placed 154.3 grams (1.67 moles) of n-butyl chloride and the reactor and contents were heated with the heating mantle until the hexane was at reflux (67.0 ° C.). The reaction mass was moderatly stirred throughout halide addition and post reaction times. A dropwise addition of n-butyl chloride was begun which brought about a vigorous reflux within 5 minutes which indicated initiation of reaction. The remaining n-butyl chloride was added dropwise to the reactor in 120 minutes which due to the exothermic reaction maintained the internal reaction temperature at reflux. The reaction mass was stirred an additional 180 minutes of post reaction time. As product formed the internal temperature gradually rose from 66.0° to 70.7 ° C. during the reaction time. The liquid portion of the reaction mass containing by-product lithium chloride was pressure pumped to a filter and then filtered. The metal remaining in the reactor was washed with a 100 milliliter aliquot of dry hexane which was also filtered and then combined with the main filtrate. The unused lithium was left in the reactor for further reactions.

A total weigh of 369.5 grams of a pale yellow solution of 15.92 wt % n-butyllithium in hexane was obtained. The recovered yield was 91.4% based on the amount of n-butyl chloride employed. The reaction was periodically monitored by GC of water quenched samples for side reaction formation and residual n-butyl chloride during the reaction. The GC conversion based on octane was 95.8% and an almost constant amount (7% of the feed) of the unreacted n-butyl chloride was found to be present during the halide feed. Ninty three percent of the total amount of n-butyl chloride employed had reacted during the halide addition. No n-butyl chloride was present after the post reaction time period.

EXAMPLE 5

(9071 & 9076) Series of 2 n-Butyllithium runs in Hexane Employing Bulk Lithium—No Stirring During the Reaction A reactor equipped as described in example 1, except the mechanical stirrer was not employed during the halide addition and post-reaction times, under an argon atmosphere, was charged with 70.4 grams ( 10.1 moles) of lithium metal in the form of 0.25 cm dia.×3.81 cm length rod (120 pieces) and 173 milliliters of dry hexane. The surface area of the lithium metal was calculated to be 975.4 cm2 and the mole ratio of lithium to n-butyl chloride was 6. In the addition funnel were placed 92.57 grams (1.0 moles) of n-butyl chloride and the reactor and contents were heated until the hexane was at reflux (66.7 ° C.). A dropwise addition of n-butyl chloride was bugun which brought about a vigorous reflux within 5 minutes which indicated initiation of reaction. The remaining n-butyl chloride was added dropwise to the reactor in 120 minutes. The exothermic reaction of halide with the lithium maintained the interal reaction temperature at reflux throughout the halide addition. The reaction mass was stirred an additional 150 minutes of post reaction times. As product formed the internal temperature gradually rose from 66.4° to 71.3 ° C. during reaction time. A slightly hazy liquid containing very little by-product lithium chloride was decanted and placed in a filter and pressure filtered (rapid filtration). Hexane (175 milliters) was charged to the reactor and allowed to contact the metal pieces (no stirring) for 20 minutes, then decanted and pressure filtered. The recovered yield of the first run (1 static wash) was 91.5% (GC conversion 96.3%) of a yellow n-butyllithium solution (20.82 wt %)in hexane GC indicated that 10% unreacted n-butyl chloride was found to be present during the halide feed. Ninty percent of the total amount of n-butyl chloride employed had reacted during the halide addition. No n-butyl chloride was present the after post reaction time period. Employing the unused lithium above which had most of the lithium chloride generated in the first run attached as an adherent scale and 14.0 grams of fresh lithium to replace the lithium used in the first reaction another run was carried out as above. After a 135 minute halide feed and 150 minute post-reaction time a slightly more hazy liquid containing a small amount of by-product lithium chloride was decanted, placed in a filter and pressure filtered. The recovered yield of the second run (no metal washes) was 90.7% (GC conversion 94.5%) of a yellow n-butyllithium solution (21.69 wt %) in hexane GC indicated that 14% unreacted n-butylchloride was found to be present during the halide feed. Eighty four percent of the total amount of n-butyl chloride employed had reacted during the halide addition. No n-butyl chloride was present after the post reaction time period. The unreacted lithium metal with the lithium chloride scale attached remaining in the reactor was vigorously stirred (4 minutes) and washed twice with 200 milliliter aliquots each of hexane. The stirring essentially removed the dispersed lithium chloride from the surface. Decantation and filtration yielded a clear solution containing 0.405 moles n-butyllithium or 4% of the yield of the above two reactions.

EXAMPLE 6

9104 Synthesis of n Butyllithium at High Concentration (60 wt %) Employing Bulk Metal—Stirred Reaction In order to compensate for the significant increase in volume due to the great amount of bulk lithium metal employed, and still permit the quantity of n-butyllithium prepared to remain the same as that prepared normally in the same-sized reactor using lithium dispersion (see comparison example) the concentration of n-butyllithium to be prepared in the solution at the end of the reaction was raised to 60 weight per cent.

A reactor equipped as described in Example 1 under an argon atmosphere was charged 70 grams (10 moles) of lithium metal (220 pieces) having a surface area of 975 cm 2 and 65 ml of hexane. The mixture was heated to reflux and n-butyl chloride addition begun with moderate stirring. One mole (92.6g) of n-butyl chloride was added over a period of two hours at reflux. The mixture was stirred and heated for an additional 1.5 hours, then allowed to cool. The product solution and by-product salts were transferred with the aid of 150 ml of solvent to bottles to allow the solids to settle. The supernatant solution was filtered and the settled muds washed and filtered to yield 364 g of clear solution with an n-butyllithium concentration of 15.92 weight per cent (0.905 moles). An additional salt wash yielded 0.015 moles to give a total yield of 92%.

EXAMPLE 7

(907 1 )Synthesis sec-Butyllithium in Hexane Employing Bulk Lithium—Stirred Reaction A reactor equipped as described in example 1 under an argon atmosphere, was charged with 61.0 grams (8.79 moles) of lithium metal in the form of 0.5 cm dia×5.08 cm length rod and 365 milliliters of dry hexane. The surface area of the lithium metal was calculated to be 479 cm2. Secondary butyl chloride (34.0 grams-0.366 mole) were placed in the addition funnel and the reactor and the contents were heated with the heating mantle until the hexane was at reflux (66.2 ° C.). The reaction mass was moderately stirred throughout halide addition and post reaction times. Addition of 2 milliliters of the s-butyl chloride brought about a vigous reflux within 2 minutes which indicated initiation of reaction. The remaining s-butyl chloride was added dropwise to the reactor in 30 minutes. The reaction refluxed throughout the halide addition with no added heat. The reaction mass was stirred for an additional 180 minutes. The liquid portion of the reaction mass was pumped to a filter and then filtered. The metal remaining in the reactor was washed with 60 and 50 milliliters of dry hexane which was also filtered and then combined with the main filtrate.

A total weight of 260.8 grams of a water white solution of 8.33 wt % sec-butyllithium was obtained. The recovered yield was 92.7% based on the amount of s-butyl chloride employed.

What is claimed is:

1. A process for preparing solutions of organolithium compounds comprising the steps of reacting lithium metal, in the form of cast or extruded ingots or pieces cut therefrom, with an organo halide in mole ratios ranging from 3:1 to 20:1 in a solvent selected from the group consisting of liquid hydrocarbons, alkyl ethers, and mixtures thereof under an inert atmosphere for one to ten hours with moderate stirring, cooling the resulting product, and separating the solution of the organolithium compound from the reacted lithium metal and by-product lithium chloride in the reactor.

2. The process of claim 1 in which the lithium metal pieces cut from cast or extruded ingots are of a weight greater than half a gram per piece.

3. The process of claim 1 in which the organo halide is s-butyl chloride, the solvent is a liquid hydrocarbon, the ratio of lithium metal to organo halide is 3:1 or greater, and the organolithium is s-butyllithium.

4. The process of claim 1 in which the organo halide is t-butyl chloride, the solvent is a liquid hydrocarbon, the ratio of lithium metal to organo halide is 3:1 or greater, and the organolithium is t-butyllithium.

5. The process of claim 1 in which the organo halide is n-butyl chloride, the solvent is a liquid hydrocarbon, the ratio of lithium metal to organo halide is 3:1 or greater, and the organolithium is n-butyllithium.

6. The process of claim 1 in which the organohalide is (3-t-butyldimethylsilyloxy)propyl-1-chloride, the ratio of lithium metal to organo halide is 3:1 or greater, and the organolithium is (3-t-butyldimethylsilyloxy)propyl-1-lithium.

7. The process of claim 1 in which the organohalide is 3-(t-butoxy)propyl-1-chloride, the ratio of lithium metal to organo halide is 3:1 or greater, and the organolithium is 3-(t-butoxy)propyl-1-lithium.

8. The process of claim 1 in which the organohalide is 3-(trimethylsilyloxy)-2,2-dimethyl-propyl-1-chloride, the ratio of lithium metal to organo halide is 3:1 or greater, and the organolithium is 3-(trimethylsilyloxy)-2,2-dimethyl-propyl-1-lithium.

9. The process of claim 1 in which the liquid hydrocarbon solvent is chosen from the group of pentane, hexane, heptane, cyclohexane, benzene, toluene and xylenes.

10. The process of claim 1 in which the the reaction of the lithium metal with the organo halide is carried out at the boiling point of the solvent.

11. The process of claim 1 in which the the organolithiums n-butyllithium, the liquid hydrocarbon is hexane, and the concentration of n-butyllithium is 50 weight percent or greater.

12. A process for preparing solutions of organolithium compounds comprising the steps of reacting lithium metal, in the form of cast or extruded ingots or pieces cut therefrom, with an organo halide in mole ratios ranging from 3:1 to 20:1 in a solvent selected form a group of liquid hydrocarbons under an inert atmosphere with no stirring for one to ten hours, cooling the product resulting therefrom, separating the desired organolithium solution from the unreacted lithium metal and adherent by-product lithium chloride in the reactor, providing a means of separating the resultant lithium halide-solvent slurry from the lithium metal, adding additional solvent and sufficient lithium metal to the reactor to maintain the lithium metal to organo halide ratio, and repeating the above steps a number of times.

13. The process of claim 12 in which the organo halide is n-butyl chloride, the solvent is hexane, the ratio of lithium metal to organo halide is 3:1 or greater, and the organolithium is n-butyllithium.

14. The process of claim 12 wherin the solvent and means of dislodging the adherent lithium chloride is a liquid hydrocarbon and vigorous mechanical stirring.

15. The process of claim 12 wherin the solvent and means of dislodging the adherent lithium chloride is a liquid ether and optionally, mechanical stirring.

16. The process of claim 12 wherin the solvent is dimethylacetamide and the means of disloging the adherent lithium chloride is mechanical stirring.

17. The process of claim 12 wherin the organo chloride is secondary butyl chloride.

* * * * *